United States Patent [19]

Rothman

[11] Patent Number: 4,550,020

[45] Date of Patent: Oct. 29, 1985

[54] POLYPEPTIDE FRACTIONS FROM MUSSEL FOR MEDICAL USE

[76] Inventor: Ulf S. E. Rothman, Västra Mellanvägen 2, Ljunghusen, S-236 00 Höllviksnäs, Sweden

[21] Appl. No.: 336,400

[22] PCT Filed: Apr. 29, 1981

[86] PCT No.: PCT/SE81/00130
§ 371 Date: Dec. 23, 1981
§ 102(e) Date: Dec. 23, 1981

[87] PCT Pub. No.: WO81/03124
PCT Pub. Date: Nov. 12, 1981

[30] Foreign Application Priority Data

Apr. 29, 1980 [SE] Sweden ............................ 8003253
Apr. 29, 1980 [SE] Sweden ............................ 8003256

[51] Int. Cl.$^4$ .................. C07G 7/00; A61K 39/00; A61K 35/56; A61K 39/395
[52] U.S. Cl. ................................. 424/88; 260/112 R; 424/85; 424/89; 424/95; 514/21
[58] Field of Search .................. 424/95, 85, 177, 359, 424/88, 89; 260/112 R

[56] References Cited

U.S. PATENT DOCUMENTS 3,655,875  4/1972  Schmeer ............................ 424/95

OTHER PUBLICATIONS

Biochem. Soc. Trans. 1976, 4(3), 473-475, Hardy et al.
Chem. Abstracts, vol. 63, 1965, 8908h, Schmeer et al.
Chem. Abstracts, vol. 66, 1967, 17178z, Judge.
Chem. Abstracts, vol. 72, 1970, 29217y, Liu et al.
Chem. Abstracts, vol. 85, 1976, 90466p, Hardy et al.
Chem. Abstracts, vol. 88, 1978, 35740k, Arimoto.
Biochem. J., (1978), 175, 467-477, Baido et al.

*Primary Examiner*—Howard E. Schain
*Attorney, Agent, or Firm*—Bacon & Thomas

[57] ABSTRACT

The invention relates to certain polypeptide fractions for use as an anti-microbial drug, drug compositions containing such polypeptide fractions, methods of reducing the infectivity possibilities of microbes by administering the polypeptide fractions, methods of preparing antisera using the polypeptide fraction, and a method of preparing the polypeptide fraction.

The polypeptide fractions are characterized in that they are isolated from the body fluids of mussels, in particular Mytilus species such as blue mussel (*Mytilus edulis*), and in that they are capable of biospecifically binding sialic acid. The polypeptide fractions are active against a broad spectrum of viruses, bacteria and protozoa.

10 Claims, 1 Drawing Figure

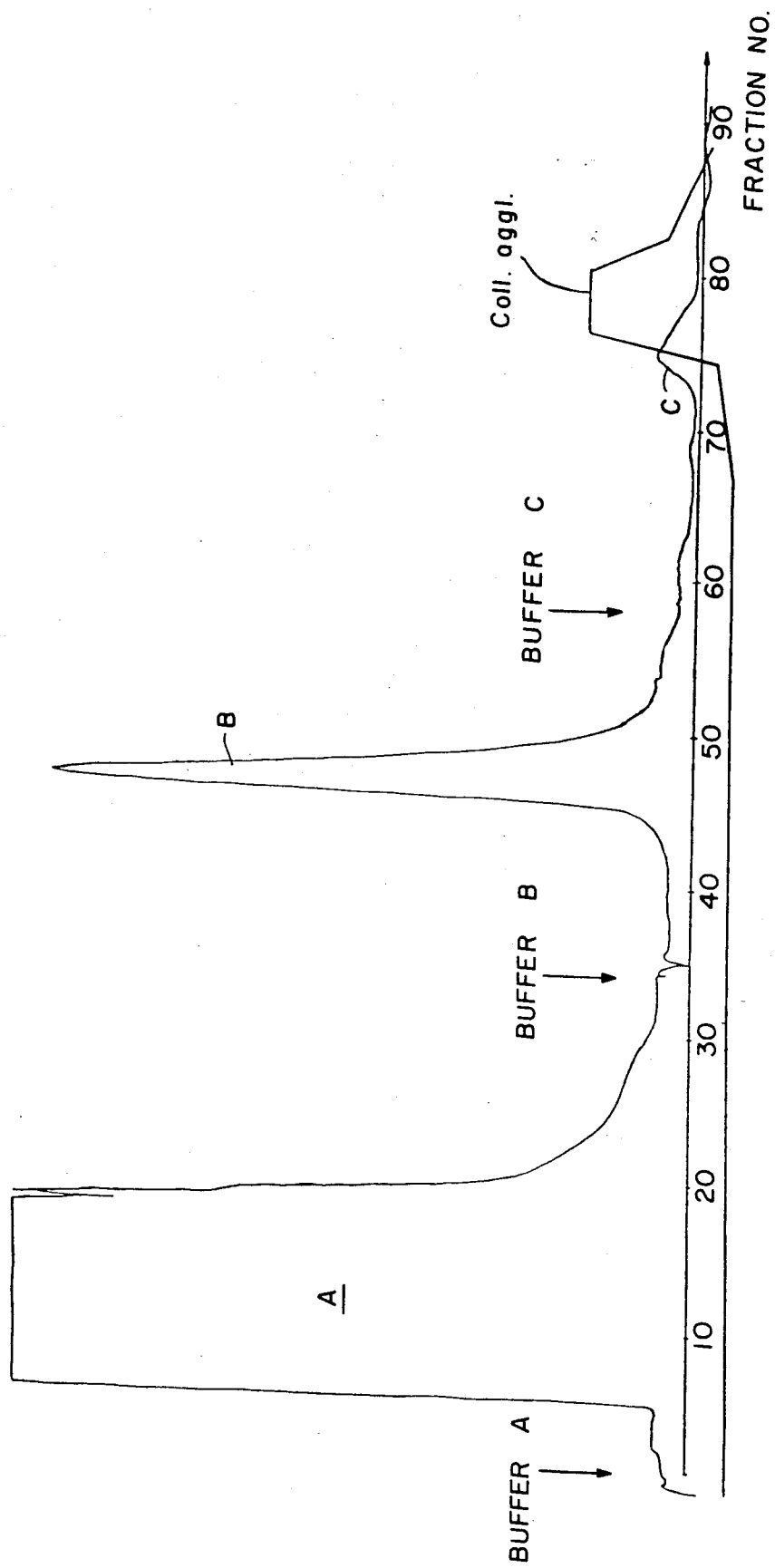

POLYPEPTIDE FRACTIONS FROM MUSSEL FOR MEDICAL USE

The present invention relates to the use as a drug of special polypeptide fractions, which can be isolated from mussels. The invention further relates to drugs containing such polypeptide fractions. More specifically the invention relates to the use of the polypeptide fractions in question as an anti-microbial drug, especially an anti-bacterial agent for prophylaxis against and treatment of bacterial infections, and as an anti-viral or immunization agent, especially as a vaccine, for example as a vaccine against myxo virus infections, such as influenza vaccine.

Epidemic influenza is a great problem which one has tried to solve by inoculation with vaccines prepared by known methods, which i.a. involve cultivation in chicken eggs. This, however, involves great difficulties since the prepared vaccines are active only against the specific virus type used. Thus, it is necessary to prepare a special vaccine for each special virus type. This is in practice most unsatisfactory since influenza virus—and other viruses—readily mutate to a new type which remains uneffected by the vaccine in question. Further, the preparation of influenza vaccines starting from live virus is complex, and the prepared vaccine contains undesired contaminants, which cause undesired side effects and may reduce the immunization effect that can be obtained. These problems have partly been solved in that methods have been developed for isolating immunogenic components from influenza virus, haemagglutinin and neuraminidase: see e.g. U.S. Pat. No. 4,064,232. Although part of the drawbacks of conventional influenza vaccines have been eliminated by this method, the problem still remains that the effect of the vaccine is restricted to a special virus type. Furthermore, the method of preparation is complex, and it is also in this case necessary to work with live viruses.

Bacterial infections are frequently occurring and also form a problem which is difficult to solve. For example, wound infections of various pathogenous bacterial strains form a most feared complication in various types of surgery ("hospital disease"). This problem is biggest in deep cavities and wounds, which makes it extremely difficult to conduct conventional treatment with antibiotics. Further, many bacterial strains have developed resistance to antibiotics by mutation. For many antibiotics the effect is also restricted to a narrow spectrum of bacteria. So far no satisfactory solution to these and similar problems have been found. The same is applicable for infections caused by protozoa.

There is thus a great need of a drug which provides an effective immune protection against various types of viruses and which further can be produced in sufficient amounts using technologically/economically possible methods. There is also a great need of an anti-microbial drug which is active against attacks of a broad spectrum of pathogenous bacteria. The present invention aims at solving i.a. these problems.

The solution proposed according to the invention means a completely new approach of attacking these problems. In contrast to, for example, known techniques in the anti-virus field virus is not at all used, neither alive nor killed. The invention instead thereof makes use of certain polypeptide fractions, which are present in comparatively great amounts in the body fluids of mussels, in particular Mytius species. These polypeptide fractions can be isolated by comparatively simple separation methods which are known per se, such as column chromatographic separation.

The polypeptide fractions used according to the invention are characterized by their capability of binding sialic acid biospecifically in the presence of calcium ions. By this is meant that the polypeptide fraction in question should be capable of biospecifically being affinity bonded to at least one amino sugar from the group of sialic acids. The expression "sialic acids" is herein used in its generally accepted meaning, viz. as N- and-/or O-substituted acyl derivatives (e.g. acetyl and/or glycocyl derivatives) of neuraminic acid; see e.g. Sai-Sun Ng and Joel A. Dain, The natural occurence of sialic acids (1974) and the Merck Index, 9th edition, 1976. The exact chemical structure of the polypeptide fractions is not known. The expression "polypeptide fraction" is therefore in the present context not restricted to polypeptides or proteines in the strict sense, but the invention is also intended to comprise any fraction isolated from mussels, which to its major part consists of polypeptide sequences and which is capable of biospecifically affinity binding sialic acid. The polypeptide fractions used according to the invention can thus, for example, possibly comprise glycoproteins. The invention also comprises the use of such fragments or sub-units of said polypeptide fractions, which are capable of biospecifically binding sialic acid in the presence of calcium ions, the sub-units preferably being administered in the presence of calcium ions, especially when used as an anti-bacterial agent.

A crude product containing a polypeptide fraction used according to the invention, together with inactive contaminants, has previously been isolated from the haemolymph (body fluid) of i.a. the blue mussel (*Mytilus edulis*), and its ability to bind sialic acid has been described (see e.g. Hardy et al, CA 85 (1976): 90466p). However, this polypeptide fraction has neither been used nor been suggested for any practical use—for example as a drug—neither in the known crude form nor in any (hithertofore not described) purified form.

It has according to the invention unexpectedly been found that immunization with the above defined polypeptide fractions increases the resistance (immune protection) against attacks from a great number of various virus types such as myxo viruses, especially various types of influenza viruses. The polypeptide fractions in question can therefore i.a. find use as a practically ideal influenza "vaccin", since one and the same product gives protection against practically all—may be even all—types of influenza viruses, and also against other types of viruses.

It has according to the invention further unexpectedly been found that the above defined polypeptide fractions form an efficient anti-microbial agent for the treatment of body surfaces (including body cavities, bone surfaces, etc.), the agent being active against attacks from a great number of various pathogenous bacteria and other microorganisms.

The reason why an effective protection against a broad spectrum of virus infections is obtained upon immunization by means of the above defined polypeptide fractions has not been fully clarified. The following attempt to a theoretical explanation of the mechanism for the observed effect must, therefore, not be regarded as a limitation of the invention. The description of the mechanism specifically relates to influenza viruses, but it is in analogeous manner applicable also to other types of viruses.

Influenza viruses are i.a. characterized by the ability of biospecifically being bonded to sialic acid. This property is also of importance for the ability of the virus particle to multiply upon penetration of the body. In doing so the sialic acid specific virus is then coupled to various types of body cells having sialic acids in their membranes, the haemagglutinin part of the virus coupling with the sialic acid. The reason why the virus particle is capable of penetrating the cell and then starting to multiply is that the virus contains the enzyme neuraminidase, which breaks away the sialic acid groups from the cell membranes while forming a so called very small hole. Because of the multiplication of the virus in the cell, the patient will get the usual influenza symptoms and the subsequent development of the disease. At the same time the body also forms antibodies against the virus in question, and part of these antibodies are directed to the haemagglutinin on the virus surface, so called anti haemagglutinin anti-bodies. In a later infuenza attack of the same virus type these antibodies will cross-react with the haemagglutinin on the virus. The result of this cross-reactivity is that the haemoglutinin of the virus is inhibited in its attempts to couple with the sialic acid on the cells. An analogeous reaction mechanism applies to inoculation against influenza by means of conventional influenza vaccine. Upon injection of such a vaccine the body forms i.a. antibodies directed against the haemagglutinin of the virus in question. On such inoculation a relatively good protection against the virus in question is obtained, however not as lasting as upon a virus infection.

Upon injection according to the invention of a sialic acid specific polypeptide fraction of the above indicated type the body will form antibodies directed against the polypeptide fraction. Part of these antipolypeptide-antibodies will, in corresponding manner as in a usual influenza attack or in conventional inoculation, cross react with the haemagglutinin on the attacking virus and in analogeous manner prevent the virus haemagglutinin from binding to the sialic acid groups which are present on various types of cells in the body. Probably because the polypeptide fraction originates from very rudimentary animals, the antipolypeptide-antibodies in question will not be specific for any special virus, but they will cross react with the haemagglutinin of a broad spectrum of viruses. The ability of the polypeptide fractions to cross react with vaccines against various types of viruses has been demonstrated in animal tests, which are reported below.

Immunization agents according to the invention, containing the above defined polypeptide fractions, can be used for prophylactic purposes for preventing the occurence of virus infections, but also curatively during an ongoing state of illness. The agent can then be administered as in conventional inoculation, i.e. by e.g. parenteral, preferably subcutaneous, injection of the polypeptide fraction together with any suitable inert liquid diluant, for example in a physiological isotonic solution, e.g. 0.9% physiological saline solution which may be buffered by means of e.g. phosphate buffer. If required various additives, such as preservatives, can be added to the agent in a manner known per se. The agent can also contain conventional immunologic adjuvants such as aluminum hydroxide or aluminum phosphate, etc. On parenteral injection of the polypeptide fractions according to the invention doses between 1 $\mu$g and 1 g are usually satisfactory. When required the injection can be repeated with intervals of one or a few weeks, using e.g. the same dose. It is preferred to inject the polypeptide fractions according to the invention in the form of a suspension in said inert liquid diluant. This can, for example, be done by adjusting the pH to the isoelectric point, a turbidity or suspension being obtained. A suitable alternative is to administer the polypeptide fraction as a depot preparation, for example by binding to a carrier such aluminum hydroxide, as is well known for other vaccins.

It has according to the invention also unexpectedly been found that the polypeptide fractions in questions also provide an efficient local immune protection against virus infections in the upper air or mucous ducts (including the lungs) upon topical application, for example in the form of a spray. On such application the agent according to the invention can be used prophylactively as well as curatively during on ongoing infection. A preferred mode of administration is nasal application, i.e. spraying in the nasal/mouth cavity, with a preferred dosage of 1 to 1000 $\mu$g once a day for 5 to 10 days. The effect can in this case be conceived to occur by at least two different reaction mechanisms.

Upon prophylactic treatment by repeated nasal application the polypeptide fraction according to the invention will form locally acting antibodies, and some of these will cross react in analogy with the above mechanism description and prevent an attacking virus from attacking the sialic acid groups which are necessary for the virus to be able to survive and multiply. During an ongoing virus infection application of the agent according to the invention can also rapidly form such antibodies and thereby moderate the ongoing development of the disease. An additive effect can be conceived to occur by a reaction mechanism which implies that the sialic acid specific polypeptide fraction according to the invention on local application is bonded to the sialic acid groups on the cells in the saliva and the nasal and mouth secreta, etc, which are frequent in the air ducts. The sialic groups of the body cells would thereby be "blocked" and as a result prevent or reduce the capability of the haemagglutinin on the virus particles to be bonded to the sialic acid groups, which is a prerequisite for the growth of the virus. This mechanism is not any immunologic reaction in the proper sense, but rather implies a direct "coating" of the cell surface by the binding to the sialic acid groups thereof.

The reason why an effective protection against attacks—ongoing or expected—of a broad spectrum of bacteria upon treatment of body surfaces with the above defined polypeptide fractions is not either fully clarified. Not either the following attempt to a theoretical explanation of the mechanism for the observed effect must therefore be regarded as any restriction of the invention.

The very reaction mechanism for the binding of pathogenic bacteria to wound surfaces and the like is relatively unknown, but this probably takes place via some kind of coupling involving sialic acid. It is known that all pathogenic bacteria in their cell membrane have i.a. sialic acid, and in their contact plate ("attachment" group) they probably also have some kind of haemagglutinins binding some sialic acid derivative. When applying the sialic acid specific polypeptide fractions from mussels according to the invention on, for example, fresh operation wounds, these fractions therefore probably are bonded to the sialic acid groups of the cells. Thereby the pathogenic bacteria invading the wound will not be able to be bonded to the cells (since the same are already "blocked" by the polypeptide fraction). This means that the bacteria cannot multiply but will die, which in turn results in the wound healing more rapidly.

If there already is a bacterial infection in a wound, treatment with the sialic acid specific polypeptide fraction according to the invention probably creates a pronounced competition between the sialic acid specificity of the polypeptide and the specificity of the bacteria. A further possible explanation is that the polypeptide fractions practically completely inhibit the ability of the bacteria to react further with the cell wall by making the bacteria (having sialic acid in their membrane) agglutinate.

On treatment of wounds and other body surfaces, the polypeptide fractions are preferably applied topically on the respective body surface in the form of a solution in any suitable diluant, for example in physiological saline solution or sterile water. In doing so it is preferred to use a freeze dried preparation, which is dissolved in the diluant in connection with the application, which e.g. can take place by brushing or spraying. The treatment can preferably be performed using doses between 1 μg and 1 g 1 to 3 times daily until the infection has been stopped.

Upon treatment of intestinal infections (caused by pathogenic bacteria or protozoa such as giardiasis, amoebiasis, entamoeba histolytica) with the polypeptide fractions according to the invention, similar reaction mechanisms as in wound treatment, etc. can be conceaved. In the intestine there are normally *E. coli* bacteria of various strains in free condition, i.e. which are not attached to the intestinal wall. Some *E. coli* strains have a different chemical structure making them prone to attach to the intestinal wall. On such attachment also bacterophags will attack the bacteria, endotoxines leaking out into the small/large intestine and causing conditions of diarrhea. When administering polypeptide fractions according to the invention to the intestine the same can, on the one hand, cause agglutination of the pathogenic bacteria and thereby inactivate the same and, on the other hand, block the sialic acid on the intestinal wall so that the bacteria cannot attack the same. Corresponding reaction mechanisms can also be used for e.g. bladder flushing with polypeptide fractions according to the invention in cases of urinary tract infections.

Upon treatment of intestinal infections by means of the polypeptide fractions according to the invention it is essential to ensure that the polypeptide fractions pass the stomach intact. To this end the polypeptide fraction (preferably in freeze dried form) is suitably enclosed in an acid resistant capsule, which can pass the acid gastric juice without being destroyed, but which is dissolved in the alkaline intestinal juice while releasing the polypeptide fractions. A suitable dosage is e.g. 10 μg to 1 g polypeptide fraction per capsule.

As mentioned above the sialic acid specific polypeptide fractions according to the invention are isolated from mussel, preferably from Mytilus species such as the blue mussel (*Mytilis edulis*), *Mytilus perna*, *Mytilus galloprovincialis*, *Mytilus californeanus*, *Mytilus smaragdinus*, and closely related Perna such as *Perna perna* and *Perna canaliculus*, but also other species may come into question. In the first place those species are of interest, which are sufficiently frequently occurring and readily accessible for making possible production in industrial scale. In this context one can mention Phaladidae, *Anodonta cygnea*, Dressensiidae, *Sphaerium corneum*, *Cyprina islandica*, *Macoma baltica*, river mussel, pearl mussel, Cardiidae, *Tridacna deresa*, Pectinnidae, Unionidae, *Unio pictorum*, *Mya arenacia*, Pinna, pilgrim mussel, etc.

The polypeptide fractions in question are isolated from the body fluids of the indicated animals. By body fluids is herein meant all systems of these rudimentary animals which correspond to the blood, lymphatic and gland systems of higher animals. One method of isolation, which is most often convenient, is to form an extract of these body fluids and to separate, possibly after suitable working up, the desired polypeptide fraction by affinity chromatography, for example in analogy with the method of isolation reported below for blue mussel especially. The purified sialic acid specific polypeptide fraction is suitably packaged as a freeze dried product in one-shot doses, and the freeze dried product can be dissolved in any suitable diluant in connection with the administration.

The invention will be described in more detail in the following working examples which, however, in no way are intended to limit the scope of the invention.

EXAMPLE 1

Live blue mussels (*Mytilis edulis*) were opened and all liquid and mussel tissue were transferred to a centrifuge vessel, which was centrifugated at 4° C. and 9,000 rpm for 40 minutes. The supernatant was collected and heated to 45° C. for 30 minutes to destroy lytic effect. The solution obtained was again centrifugated at 4° C. and 9,000 rpm for 30 minutes. The supernatant was collected and saturated ammonium sulphate solution was added to a saturation concentration of 65%. The precipitate obtained was kept at room temperature for 30 minutes and was then centrifugated at 9,000 rpm for 30 minutes. The supernatant was discarded and the precipitate was dissolved in 0.05M phosphate buffer pH 7.4, 0.05M sodium chloride (PBS) and was dialyzed against PBS. A freeze dried sample of the product was colourless and readily soluble in distilled water.

1.0 mg of bovine submaxillary mucin (which contains sialic acid) was coupled in a manner known per se to 30 g of bromocyane activated Sepharose ®4B (agarose, available from Pharmacia Fine Chemicals, Uppsala, Sweden). The formed gel was then packed in a gel filtration column and equilibrated with 0.05M tris-HCl, 0.1M sodium chloride, 0.01M calcium dichloride buffer, pH 8.5. 40 ml of the polypeptide fraction, prepared and dialyzed as described above, were applied to the column, which was eluted with the said buffer (buffer A in the enclosed drawing). The eluate from the column was followed by absorbtion at 280 nm and collected in fractions. After a main fraction of the proteins had been eluted (see the peak A in the drawing) the elution buffer was changed to 0.05M tris-HCl, 1.0M NaCl, 0.01M calcium dichloride buffer, pH 8.5 (buffer B in the drawing). With this buffer a number of protein fractions were eluted—see the peak B in the drawing. Finally, the column was eluted with 0.05M tris-HCl, 1.0M NaCl buffer, pH 8.5 (buffer C in the drawing), a minor amount of protein being eluted—see the peak C in the drawing. The collected fractions (A, B and C) were examined with regard to haemagglutinating effect. The haemagglutination test was carried out according to the method described by Hammarström, S. and Kabat, E. A. in Biochemistry 8, 2696 (1969). Micro titer plates and a 2% solution of human erythrocytes belonging to different blood groups in 0.9% sodium chloride were used. Only the fraction C agglutinated red blood cells, i.e. was sialic acid specific (see the curve "Coll. aggl." in the drawing).

The active polypeptide fraction C was concentrated 10 times by ultra filtration (Amicon UM 10 filter) and dialyzed to equilibrium against 0.05M tris-HCl, pH 8.5, 0.15M sodium chloride, 0.003M calcium chloride buffer. After freeze drying a colourless product was obtained, which was readily soluble in water.

The molecular weight of the isolated sialic acid specific fraction was determined by SDS-polyacrylamide electrophoresis using the gradient gel PAA4/30 and a molecular weight calibration kit (from Pharmacia Fine Chemicals, Uppsala, Sweden). The electrophoresis showed four bands within the molecular weight range: 14,500–30,000. These bands in the electrophoresis probably originate from so-called subgroups of a larger protein, which can be re-formed by recoupling of the subgroups in the presence of calcium ions.

The amino acid composition was investigated by conventional amino acid analysis. The results are reported in the following table. No amino sugar could be detected:

| Amino acid | % | Amino acid | % |
|---|---|---|---|
| Asp | 16.5 | Met | 0.4 |
| Thr | 5.5 | Ile | 4.3 |
| Ser | 8.3 | Leu | 5.2 |
| Glu | 10.8 | Tyr | 9.6 |
| Pro | 3.3 | Phe | 5.6 |
| Gly | 5.1 | His | 3.8 |
| Ala | 2.0 | Lys | 7.3 |
| Val | 4.4 | Arg | 7.7 |

The isoelectric point of the polypeptide fraction was 4.6.

EXAMPLE 2

A preparation suitable for subcutaneous injection was prepared by dissolving 150 μg of the freeze dried product according to Example 1 in 0.5 ml of distilled water and adjusting the pH to 4.6 (turbidity).

EXAMPLE 3

A preparation suitable for nasal application can be prepared by dissolving 50 to 100 μg (one-shot dose) of freeze dried polypeptide fraction according to Example 1 in 1 to 1.5 ml of sterile distilled water. The preparation is filled on a spray bottle and is preferably applied by spraying without propellant gas. Multidose packages can be prepared by proportionally increasing the amount of polypeptide fraction and diluant.

EXAMPLE 4

The haemagglutination inhibiting effect upon immunization with the polypeptide fractions used according to the invention was investigated in the following way.

2 mg of freeze dried polypeptide fraction (prepared according to Example 1) was suspended in 0.4 ml of physiological saline solution (0.9%) plus 0.5 ml of Freunds adjuvant and was injected subcutaneously in multiple injections at the back of two rabbits (3 kg each). Fourteen days later another 2 mg were injected in the same manner in each rabbit, i.e. in total 4 mg of polypeptide fraction per rabbit. Blood samples were taken before the first injection and 3 weeks thereafter, and the serum samples were examined on Ouchterlony plates. It turned out that precipitation occurred between the polypeptide fraction and the 3 week serum. In contrast thereto no precipitation occurred with serum taken before the immunization. Each rabbit thus served as its own control.

The three-week serum was then examined by means of a conventional haemagglutination inhibition test. The following polyvalent influenza vaccines were used as virus sources: (1) A-USSR-90,92,97-77(H1N1), (2) A-England-864-75(H3N2), and (3) B-Hongkong-8-73. One ml of the vaccine contains 50 μg of haemagglutinin. The test is carried out by mixing, on an object glass, one drop of vaccine suspension, one drop of three-week serum from the immunized rabbits, and one drop of (carefully washed) dog erythrocytes suspended in physiological saline solution (2% w/v suspension). One drop of 0.15M phosphate buffer and zero serum respectively (i.e. serum samples taken before the immunization) from the rabbits were used as controls instead of one drop of three-week serum.

No haemagglutination at all occurs with three week serum from the immunized rabbits, whereas haemagglutination takes place immediately (within 1 min.) in all of the controls. There is no difference between the two rabbits. These results clearly indicate that the injection of the polypeptide fraction according to the invention has caused formation of antibodies, which are active against a broad spectrum of viruses.

EXAMPLE 5

A preparation suitable for wound treatment is prepared by dissolving 200 μg freeze dried polypeptide fraction from Example 1 in 1.5 ml sterile water or physiological saline solution.

EXAMPLE 6

A preparation suitable for oral treatment of intestinal infections is prepared by enclosing the freeze dried polypeptide fraction from Example 1 in acid resistant capsules, which pass the acid gastric juice essentially uneffected but are dissolved in the alkaline environment in the small and large intestine while releasing the enclosed polypeptide fraction. A suitable dosage is e.g. 200–300 μg/capsule.

EXAMPLE 7

On two Sprague-Dawley rats (400 g) two wounds were cut on the back down to the fascia (surface ~2.8 cm$^2$). In order to prevent contamination simple wound rings were attached by sewing and glued to the edge of the wound. One of the wounds was treated with 0.2 ml of 0.1% solution of the polypeptide fraction isolated according to Example 1, whereas the other wound was treated with 0.2 ml of 0.9% physiological saline solution. Transparent caps permitting inspection of the wounds were attached by screwing on the two wound rings in order to prevent contamination. Every day during 5 days the wounds were treated with 0.2 ml of polypeptide solution and 0.2 ml of physiological saline solution respectively. Using a gelatine syringe samples were taken on days 1, 4, 6 and 8 from the wound surfaces in order to determine the bacterial contents. Physiological saline solution was added to the samples, which were incubated in a 37° C. water bath for 15 minutes. Dilution series of the samples were applied to agar plates which were incubated at 37° C. over night. The number of colonies was counted. At the same time the wound healing process was observed. No significant difference was noticed as to the bacterial contents. In contrast thereto a better and more rapid healing process was observed for the wound that had been treated with the polypeptide solution.

EXAMPLE 8

3 cm² large wounds were cut on the back of four Sprague-Dawley rats. On two of the rats the wounds were washed with 0.2 ml of 0.1% solution of the freeze dried product prepared according to Example 1. After 15 minutes the wounds were again washed with this solution and after another 15 minutes with 0.1 ml of the solution. The wounds on the other two rats were washed with corresponding amounts of 0.9% physiological saline solution at corresponding times.

20 minutes after the last washing all wounds were infected with $1.7 \times 10^4$ of the bacteria *Pseudomonas aerigunosa*. For the two test rats the wounds were treated 3 times a day with 0.2 ml of polypeptide fraction solution, but the control rats with 0.2 ml of physiological saline solution, for four days. The general condition of the rats was observed daily for seven days. As a result of the infection the control rats exhibited nose bleeding, weight reduction and generally bad health condition, whereas the treatment group exhibited unchanged general condition.

EXAMPLE 9

In the same manner as in Example 1 haemolymph from M.edulis was collected and heat treated, and the precipitate obtained was removed by centrifugation. 15 ml of 0.2M tris-HCl buffer, pH 9.3 were added to the thus heat treated haemolymph, the pH of the mixture being measured to 8.5 (this pH should be in the interval 8 to 9). The solution was cooled with magnetic stirring to −5° C. 15 ml of cooled 53% ethanol was then added with magnetic stirring by means of a peristaltic pump at a rate of 23.2 ml/h, a precipitate being formed. The suspension was kept with magnetic stirring at −5° C. for another 30 minutes. The suspension was then centrifugated at 9,000 rpm for 30 minutes at −5° C. The centrifugated precipitate was at room temperature suspended in 6 ml of 0.15M sodium chloride solution. The suspension was centrifugated at 20,000 rpm for 20 minutes at 4° C. The centrifugated solution, the pH of which was 8.0, was filtered through a 0.22μ filter and freeze dried. The sialic acid binding ability of the prepared extract was determined by the ability to agglutinate a 2% suspension of human red blood cells in 0.15M of sodium chloride solution. Visible agglutination was still observed at 256 times dilution (1:256) of the extract.

I claim:

1. A vaccine against viral infections comprising an anti-viral amount of a polypeptide fraction isolated from the body fluids of the Mytilus species of mussels consisting essentially of a fraction of the body fluids which is capable of biospecifically binding at least one sialic acid in the presence of calcium ions, and wherein said fraction has been obtained by forming an extract of the Haemolymph from the mussel which was subjected to separation with regard to sialic acid binding capability, and a pharmaceutically acceptable carrier.

2. The vaccine of claim 1, wherein the viral infections against which the composition is effective is caused by myxo viruses.

3. A nasal spray containing a polypeptide fraction isolated from the body fluids of the Mytilus species of mussels consisting essentially of a fraction of the body fluids which is capable of biospecifically binding at least one sialic acid in the presence of calcium ions, and wherein said fraction has been obtained by forming an extrant of the Haemolymph from the mussel which was subjected to separation with regard to sialic acid binding capability, dissolved in distilled water and contained in a spray bottle without propellant gas.

4. A capsule for oral treatment of intestinal infections which capsule is acid resistant and will pass the acid gastric juice essentially uneffected but will dissolve in the alkaline environment in the small and large intestine and which capsule contains a polypeptide fraction isolated from the body fluids of the Mytilus species of mussels consisting essentially of a fraction of the body fluids which is capable of biospecifically binding at least one sialic acid in the presence of calcium ions, and wherein said fraction has been obtained by forming an extract of the Haemolymph from the mussel which was subjected to separation with regard to sialic acid binding capability, and which is present in an amount effective to prevent or inhibit bacterial attacks in the intestines.

5. A method of providing effective local immune protection against virus infections in the upper air or mucous ducts by topically applying thereto an effective amount of a polypeptide fraction isolated from the body fluids of the Mytilus species of mussels consisting essentially of a fraction of the body fluids which is capable of biospecifically binding at least one sialic acid in the presence of calcium ions, and wherein said fraction has been obtained by forming an extract of the Haemolymph from the mussel which was subjected to separation with regard to sialic acid binding capability, in a pharmaceutically acceptable carrier.

6. The method of claim 5, wherein the pharmaceutically acceptable carrier is sterile distilled water and the form of topical application is by nasal spray.

7. A method of treating intestinal infections caused by pathogenic bacterial or protozoa which comprises orally administering the composition of claim 4 to a patient in need thereof.

8. A method of treating wounds prophylactically or treating infected wounds which comprises applying topically to the wound an effective amount of a polypeptide fraction isolated from the body fluids of the Mytilus species of mussels consisting essentially of a fraction of the body fluids which is capable of biospecifically binding at least one sialic acid in the presence of calcium ions, and wherein said fraction has been obtained by forming an extract of the Haemolymph from the mussel which was subjected to separation with regard to sialic acid binding capability, in a pharmaceutically acceptable carrier.

9. The method of claim 8, wherein the wounds are surgical wounds.

10. A vaccine against viral infections comprising an anti-viral amount of a polypeptide fraction isolated from the body fluids of the Mytilus species of mussels consisting essentially of a fraction of the body fluids which is capable of biospecifically binding at least one sialic acid in the presence of calcium ions, and wherein the polypeptide fraction was obtained by forming an extract of the Haemolymph from the mussel, which was subjected to heat treatment to destroy the lytic effect, and subjected to affinity chromatographic separation with regard to the sialic acid binding capability, and a pharmaceutically acceptable carrier.

* * * * *